United States Patent [19]

O'Hara et al.

[11] Patent Number: 4,490,571
[45] Date of Patent: Dec. 25, 1984

[54] OLIGOMERIZATION OF OLEFINS

[75] Inventors: Mark J. O'Hara; Tamotsu Imai, both of Mount Prospect, Ill.

[73] Assignee: UOP Inc., Des Plaines, Ill.

[21] Appl. No.: 539,208

[22] Filed: Oct. 5, 1983

[51] Int. Cl.$^3$ .................................................. C07C 2/02
[52] U.S. Cl. ...................................... 585/525; 585/527
[58] Field of Search .................................. 585/525, 527

[56] References Cited

U.S. PATENT DOCUMENTS

| | | | |
|---|---|---|---|
| 3,109,041 | 10/1963 | Child et al. | 260/683.15 |
| 3,997,621 | 12/1976 | Brennen | 585/525 |
| 4,048,108 | 9/1977 | Ryu | 252/442 |
| 4,048,109 | 9/1977 | Ryu | 252/442 |
| 4,108,920 | 8/1978 | Ryu | 260/683.15 B |
| 4,110,410 | 8/1978 | Ryu | 260/683.15 B |
| 4,308,414 | 12/1981 | Madqaukar et al. | 585/525 |

FOREIGN PATENT DOCUMENTS 734264 10/1952 United Kingdom .

Primary Examiner—Curtis R. Davis
Attorney, Agent, or Firm—James R. Hoatson, Jr.; Raymond H. Nelson; William H. Page, II

[57] ABSTRACT

An oligomerization process is effected by treating olefinic hydrocarbons containing from 2 to about 6 carbon atoms in the presence of a catalyst comprising boron fluoride composited on an alumina support. The catalyst is treated with an additive comprising an oxygen or nitrogen-containing compound either prior to or during the process whereby the product which is obtained from the reaction will contain oligomer isomers possessing minimal branching.

19 Claims, No Drawings

OLIGOMERIZATION OF OLEFINS

BACKGROUND OF THE INVENTION

In the past, various catalysts have been employed for the polymerization of olefins, said catalysts comprising those known in the art as Ziegler-Natta catalysts. These catalysts typically consist of titanium chloride which has been activated with an aluminum alkyl, said catalysts operating in the form of a sludge or slurry. For example, titanium tetrachloride may be used in conjunction with an organic compound such as triethylaluminum or other organoaluminum compounds. The titanium tetrachloride is reduced to a lower valent titanium chloride by the organoaluminum compound. A variation of this type of catalyst comprises impregnation of alumina with a titanium tetrahalide followed by reduction with hydrogen at elevated temperatures or by reduction effected by contact with a solution or dispersion of a reducing agent such as an alkali or alkaline earth metal halide, etc. However, these catalysts are useful in polymerizing olefins to form solid polymers, and specifically, high molecular weight solid polymers in which the molecular weight will range from 300 to 100,000. Catalysts of this type is preparing solid polymers usually employ aromatic hydrocarbons such as benzene, toluene, xylene as suitable diluents. The use of a diluent such as an aromatic hydrocarbon may not be employed when utilizing the heterogeneous oligomerization catalyst which is used in the present process inasmuch as the aromatic hydrocarbon, if present, would enter into the reaction in which parts or all of the olefin would act as an alkylating agent rather than as a monomer in the polymerization reaction.

Other catalysts which have been used for polymerizing olefins also comprise titanium tetrahalides composited on a solid support such as an alumina, the finished composite having been prepared in various ways such as by activating alumina at an elevated temperature followed by treating the activated base with a mixture of an inert gas and titanium tetrachloride or by treating an alumina gel with fluotitanic acid. As was previously stated, these catalysts may be employed to polymerize olefins to heavier hydrocarbons, that is, solid polymers and, in addition, may also be used to alkylate paraffins with olefins, usually at temperatures which are relatively high in nature.

Prior patents have shown various processes involving the polymerization of olefins. For example, U.S. Pat. No. 3,109,041 shows a process for polymerizing isobutylene having a molecular weight of from about 300 to about 10,000, the process involving two stages. In the first stage, butylene is reacted in admixture with an inert solvent in contact with a Friedel Crafts catalyst in the absence of a support. The second stage involves the reaction in the presence of a fixed bed supported Friedel Crafts catalyst with the purpose of obtaining total polymerization. British Pat. No. 734,264 utilizes a catalyst which is chemisorbed on a binary or tertiary gel such as silica-alumina, silica-magnesia, silica-zirconia, etc., silica-aluminamagnesia, etc., the objective of the process being the production of gasoline.

In addition to these patents, two other U.S. patents also teach a process for oligomerizing olefinic compounds. U.S. Pat. No. 4,108,920 utilizes, as a catalyst for the reaction, a compound which has been prepared by heating a metal oxide which possesses surface hydroxyl groups with hydrogen and nitrogen at an elevated temperature which may range from about 350° to about 550° C. and thereafter impregnating the heated metal oxide with a solution of titanium tetrafluoride. The impregnated oxide is then cold-rolled, followed by steam drying and further drying the component at an elevated temperature of from about 200° to about 600° C. in an inert atmosphere. Likewise, U.S. Pat. No. 4,110,410 also discloses a process for the oligomerization of olefins using a catalyst which has been prepared by heating a metal oxide again possessing surface hydroxyl groups at a temperature in the range of from about 400° to about 600° C., contacting the metal oxide with a titanium tetrachloride vapor in a series of steps at progressively higher temperatures whereby the titanium tetrachloride is composited on the metal oxide. The impregnated metal oxide is then heated in contact with hydrogen at elevated temperatures ranging from about 300° to about 700° C. to reduce the titanium to a valence state of less than +4 and thereafter using this catalyst to oligomerize olefins. U.S. Pat. Nos. 4,048,108 and 4,048,109 disclose methods for preparing the catalysts which are utilized in the aforementioned two U.S. patents. However, the process using these catalysts results in a product mix which is heavy in highly branched-chain products. As will hereinafter be shown in greater detail, by utilizing the catalysts of the present invention, it is possible to obtain selective oligomers of olefinic hydrocarbons, the oligomers being selectively less branched compounds.

SUMMARY OF THE INVENTION

This invention relates to a process for the oligomerization of olefinic hydrocarbons. More specifically the invention is concerned with a process for the oligomerization of olefinic hydrocarbons employing a specific step in the process whereby increased yields of selective oligomers of the olefinic feedstock may be obtained.

Many olefinic hydrocarbons which contain from 4 to about 12 carbon atoms in the chain are utilized in various industries in many ways. For example, one specific use of these hydrocarbons and especially hydrocarbons containing 8 carbon atoms in the chain, is as a component in motor fuels, such as internal combustion engines utilizing gasoline or engines using diesel fuel. The presence of these compounds in motor fuels will improve the octane number of the fuel to a higher level, thus enabling the motor fuel such as gasoline to produce a relatively higher octane number, either in the leaded or unleaded state. Another use of such compounds would be as plasticizers, especially those olefins which possess a relatively straight-chain configuration with a minimum of branching such as 1 or 2 methyl substituents on the chain. These compounds will find use, as hereinbefore set forth, as plasticizers which, when added to a plastic, will facilitate compounding and improve the flexibility and other properties of the finished product. Examples of uses for olefins containing 6 carbon atoms would be in the synthesis of flavors, perfumes, medicines, dyes and resins, while olefins containing 12 carbon atoms may be used as intermediates in the preparation of detergents, lubricants, additives, plasticizers, in the synthesis of flavors, perfumes, medicines, oils, dyes, etc.

It is therefore an object of this invention to provide a process for the oligomerization of olefinic hydrocarbons.

A further object of this invention is to provide a process for the oligomerization of olefinic hydrocarbons utilizing a specific catalyst system whereby selective oligomers may be obtained thereby.

In one aspect an embodiment of this invention resides in a process for the oligomerization of an olefin which contains from 2 to about 6 carbon atoms which comprises oligomerizing said olefin at oligomerization conditions in the presence of a catalyst comprising boron fluoride composited on an inorganic oxide and recovering the resultant oligomer, the improvement which comprises treating said catalyst with an oxygen or nitrogen-containing organic compound.

A specific embodiment of this invention will be found in a process for the oligomerization of butene-2 which comprises oligomerizing said butene-2 at a temperature in the range of from about 50° to about 300° C. and a pressure in the range of from about 100 to about 1500 pounds per square inch gauge (psig) in the presence of a catalyst comprising a boron fluoride composited on gamma-alumina, said catalyst having been treated with from about 10 ppm to about 5% by weight of dimethyl ether, and recovering the selective oligomers comprising a mixture of methyl heptene, dimethyl hexene, and trimethyl pentene.

Other objects and embodiments will be found in the following further detailed description of the invention.

DETAILED DESCRIPTION OF THE INVENTION

As hereinbefore set forth, the present invention is concerned with a process for the oligomerization of olefinic hydrocarbon containing from 2 to about 6 carbon atoms, said oligomerization being effected in the presence of a catalyst of the type hereinafter set forth in greater detail which has been subjected to treatment with an oxygen or nitrogen-containing compound to obtain selective oligomers. The term "polymerization" has a relatively broad meaning in the chemical arts. Although it is generally referred to as the preparation of relatively high molecular weight polymers, it may also refer to the preparation of low molecular weight polymers. In contradistinction to this, the term "oligomerization" refers to polymeric compounds in which the molecules consist of only a relatively low number of monomeric units and would include dimerization, trimerization or tetramerization, that is, molecules containing 2, 3 or 4 monomeric units. In view of the unpredictable art of catalysis, it was totally unexpected that by utilizing the catalyst composition of matter comprising boron trifluoride composited on a refractory inorganic oxide support which has been subjected to treatment with certain compounds of the type hereinafter set forth in greater detail, it would be possible to obtain selective oligomers which possess a minimum amount of branching. This result was even more unexpected in view of prior references including those patents previously discussed utilizing titanium fluoride as a catalyst which produced oligomers possessing a relatively high degree of branching. Therefore, the process of this invention, utilizing a catalyst hereinafter more fully described which has been treated with certain types of organic compounds, contrasts with the process of the prior references, inasmuch as the treated catalyst of the present invention possesses different capabilities and functions in performing its catalytic duty. Olefinic hydrocarbons which may be used as the feedstock and which may undergo oligomerization according to the process of this invention comprise those olefins containing from about 2 to about 6 carbon atoms such as ethylene, propylene, butene-1, butene-2, pentene-1, pentene-2, hexene-1, hexene-2, hexene-3, etc. It is also contemplated within the scope of this invention that branched chain isomers of these olefins as well as olefins containing more than 6 carbon atoms may also undergo oligomerization, although not necessarily with equivalent results.

The catalyst system which is used to effect the oligomerization of the aforementioned olefins comprises boron fluoride supported on an inorganic oxide. The boron fluoride may be present on the support in a range of from about 1 to about 20% by weight of the catalyst. In the preferred embodiment of the invention, the metal oxide which is utilized will comprise alumina, and particularly a high surface area alumina such as gamma-alumina, or, if so desired, eta-alumina or other forms of alumina. The Apparent Bulk Density of the alumina may range from about 0.2 to about 0.7 g/cc or higher and will possess a surface area ranging from about 1 to about 500 m$^2$/g. The shape of the support may be in various forms such as spheres, pellets, rods, etc. It is also contemplated within the scope of this invention that other metal oxides may also be employed as solid supports, some representative examples of these supports will include silica, or mixtures of inorganic oxides such as silica-alumina, silica-magnesia, silica-zirconia, silica-thoria, silica-magnesia-zirconia, etc. Further supports which may be used, although not necessarily with equivalent results, will include solids such as charcoal, coal, diatomaceous earths and clays such as fullers earth, bentonite, montmorillonite, kieselguhr, etc. It is to be understood that these compounds will act only as supports for the catalyst system and will not enter into the catalytic activity of the composite.

The catalyst which is utilized to effect the oligomerization in the present process whereby selective oligomers containing a minimum of branching are obtained may be prepared by subjecting the inorganic oxide which is utilized as a support to a drying step at an elevated temperature. Temperatures which may be employed to effect this drying step may range from about 400° to about 700° C. Following the calcination of the support, it may then be further dried at lower temperatures which may range from about 250° to about 350° C. until the water content of the support reaches a predetermined level. The support is then contacted with the boron fluoride, usually at an elevated temperature in the range of from about 350° to about 400° C. for a period of time sufficient to impregnate the base with the desired amount of catalyst, that is, from about 1% to about 20% by weight. Following the impregnation of the support, the catalyst may then be cooled and maintained, preferably in an inert atmosphere to minimize any adsorption of moisture until use.

The aforementioned catalyst, in order to obtain the desired selective oligomers of olefins which contain a minimum of branching, is treated with an oxygen or nitrogen-containing organic compound, said treatment being effected prior to loading the catalyst into the predetermined oligomerization vessel, during the start-up of the oligomerization process or in situ at any period during the oligomerization process to produce the desired product distribution. Depending upon the particular effect which is desired to be obtained, the catalyst may be treated with the oxygen or nitrogen-containing compound in an amount in the range of from about 10 parts per million (ppm) up to about 5% by weight of the catalyst. Examples of oxygen or nitrogen-containing compounds which may be employed as the additive to the catalyst will include oxygen-containing organic compounds such as alkyl ethers, either symmetrical or unsymmetrical, containing from 1 to about 4 carbon atoms in the alkyl chain. Some specific examples of these ethers will include dimethyl ether, diethyl ether, di-n-propyl ether, diisopropyl ether, di-n-butyl ether, methyl ethyl ether, methyl n-propyl ether, methyl isopropyl ether, methyl n-butyl ether, ethyl n-propyl ether, ethyl isopropyl ether, etc., unsaturated ethers such as vinyl methyl ether, vinyl ethyl ether, vinyl n-propyl ether, allyl methyl ether, allyl ethyl ether, etc., heterocyclic ethers such as furan, furfural, 1,2-pyron, 1,4-pyron, etc. Examples of nitrogen-containing organic compounds which may be employed as the additive will include alkylamines containing from 1 to about 20 carbon atoms such as methylamine, dimethylamine, trimethylamine, ethylamine, diethylamine, triethylamine, n-propylamine, di-n-propylamine, tri-n-propylamine, n-butylamine, di-n-butylamine, tri-n-butylamine, isopropylamine, diisopropylamine, triisopropylamine, t-butylamine, di-t-butylamine, tri-t-butylamine, n-pentylamine, di-n-pentylamine, tri-n-pentylamine, sec-pentylamine, di-sec-pentylamine, tri-sec-pentylamine, the isomeric hexyl, heptyl, octyl, nonyl, etc., mono-, di- and triamines, fatty amines such as n-dodecylamine, n-tallow-1,3-propane diamine, etc., cyclic amines such as morpholine, aromatic amines such as aniline, etc. It is to be understood that the aforementioned oxygen and nitrogen-containing organic compounds are only representative of the class of compounds which may be utilized as additives for treatment of the catalyst and that the present invention is not necessarily limited thereto.

The process of the present invention in which an olefinic hydrocarbon is oligomerized to obtain selective oligomers thereof may be effected in any conventional manner including both batch and continuous type operations. As an example, when a batch type operation is employed, a quantity of the catalyst is placed in an appropriate apparatus which may comprise a reaction flask, autoclave, etc., the placement of the catalyst in the reaction apparatus being effected while maintaining the catalyst in an inert atmosphere such as nitrogen, helium, argon, etc. The catalyst which is employed prior to being placed in the reaction apparatus, is treated by contact with an oxygen or nitrogen-containing organic compound of the type hereinbefore set forth for a predetermined period of time which may range from about 0.5 to about 10 hours. After this pretreatment of the catalyst has been effected, the oxygen or nitrogen-containing organic compound is removed from the catalyst prior to said catalyst being placed in the apparatus. Thereafter, the olefinic hydrocarbon which is to be oligomerized is charged to the apparatus containing the catalyst while maintaining said apparatus at predetermined reaction or oligomerization conditions which will include a temperature in the range of from about 50° to about 300° C. and a pressure in the range of from about 100 to about 1500 pounds per square inch (psig). The oligomerization reaction is allowed to proceed for a period of time which may range from about 0.1 up to about 10 hours or more in duration. Upon completion of the desired reaction period, the reaction mixture, after allowing the apparatus to return to room temperature and atmospheric pressure, is recovered and the desired products, comprising the minimal branched oligomers, are separated from the catalyst and any unreacted olefin by conventional means such as fractional distillation. It is also contemplated within the scope of this invention that the oligomerization reaction may be effected in a continuous manner. When such a type of operation is employed, the boron fluoride-supported catalyst is placed in an appropriate reaction apparatus which is maintained at the proper operating conditions of temperature and pressure within the range hereinbefore set forth. The olefinic feedstock which is to be oligomerized is continuously charged to the reaction vessel, if so desired, in admixture with a paraffinic hydrocarbon which will act as a diluent, said charge to the reaction vessel being effected at a Liquid Hourly Space Velocity within the range of from about 0.5 to about 10.0 hrs.$^{-1}$. After a predetermined reaction period has elapsed, the additive comprising the oxygen and nitrogen-containing compound is then introduced into the reaction vessel for a predetermined period of time whereby the treatment of the catalyst is effected. After charging the additive to the reaction vessel in an amount within the range of from about 10 ppm to about 5%, the addition of the additive is discontinued and the oligomerization process is continued. The reactor effluent is continuously discharged and the effluent is subjected to conventional means of separation whereby any unreacted olefins may be recycled to the reaction apparatus to form a portion of the feedstock while the desired minimal branched oligomers are recovered. Inasmuch as the catalyst which is employed in the oligomerization reaction is in solid form, various methods of continuous operation may be employed. For example, the catalyst may be positioned in the reaction appartus as a fixed bed and the feedstock and additive are passed over said catalyst in either an upward or downward flow, the only criteria being that a sufficient amount of additive is employed to completely treat the catalyst present in the reaction vessel. Another method of effecting the process is to utilize a moving bed type of operation in which the catalyst and feedstock along with the additive are passed through the reaction apparatus either concurrently or countercurrently to each other while effecting contact between the catalyst, the reactant and the additive. In addition to these methods of operation, a third method of effecting the continuous reaction may be utilized comprising the slurry type in which the catalyst is carried into the reactor as a slurry in the liquid feed, the additive being introduced to the catalyst either prior to passage into the reactor or while the catalyst is in the reaction vessel. Regardless of which type of operation is employed, the reactor effluent is continuously recovered and subjected to separation means whereby the desired minimal branched oligomers are separated and recovered.

Examples of oligomers which may be obtained by utilizing the process of the present invention in which the catalyst is treated with an oxygen or nitrogen-containing compound will include n-butene, n-hexene, 4-methyl-1-pentene, 3-methyl-1-pentene, 2-methyl-1-pentene, n-octene, the isomeric methylheptenes, dimethylhexenes, trimethylpentenes, n-decene, the isomeric methylnonenes, dimethyloctenes, trimethylheptenes-n-dodecene, the isomeric methylundecenes, dimethyldecenes, trimethylnonenes, etc.

The following examples are given for the purpose of illustrating the process of the present invention. However, it is to be understood that these examples are merely illustrative in nature and that the present process is not necessarily limited thereto.

EXAMPLE I

A catalyst for the present invention was prepared by calcining a gamma-alumina base at a temperature of 625° C. in an air atmosphere followed by purging the base with dry air at a rate of 2.65 cubic feet per hour per pound of catalyst at a temperature of 290° C. until the water content of the excess gas was less than 30 ppm. Thereafter, the base was treated with boron trifluoride introduced into the reactor at a rate of 0.035 pounds per pound of catalyst until the peak catalyst temperature reached 357° C. The catalyst was then cooled in air to a temperature of 66° C. and unloaded from the reactor.

The catalyst which was prepared according to the above paragraph was placed in a tubular reactor and a feedstock comprising a blend of 60% butene-2 and 40% n-butane was passed over the catalyst at a LHSV of 1.0 hrs.$^{-1}$ while maintaining an inlet temperature of 150° C. and a pressure of 100 psig. The results from this run showed a 51.4% conversion.

EXAMPLE II

During the same run described in Example I above, at 600 hrs. on stream, 1000 ppm of dimethyl ether was added to the feed blend, the conversion decreasing to 24.7% during a period of 72 hours. At the end of the 72 hours, introduction of the dimethyl ether was discontinued. The conversion of the butene-2 increased to 48.5% after a period of 36 hours. Analysis of the product by gas chromatography was made and the results obtained after treatment with the ether were compared with the results obtained from the process prior to introduction of the additive.

TABLE I

|  | Before DME Addition | 36 Hrs. After DME Addition |
|---|---|---|
| Catalyst Temperature, °C.: | | |
| Inlet | 150 | 153 |
| Maximum | 163 | 168 |
| % Conversion | 51.4 | 48.5 |
| Selectivity: | | |
| $C_6$ | 0.7 | 0.5 |
| $C_7$ | 0.3 | 0.4 |
| $C_8$ | 81.1 | 84.2 |
| $C_{9+}$ | 17.9 | 14.9 |
| Octene Isomers: | | |
| Methylheptene | 2.9 | 8.3 |
| Dimethylhexene | 96.9 | 91.5 |
| Trimethylpentene | 0.2 | 0.2 |

It is obvious from a comparison of the octene isomers that the treatment with the ether produced a larger amount of less branched product, that is, the amount of methylheptene produced after the ether treatment was almost three times the amount produced prior to the additive treatment.

EXAMPLE III

The oligomerization of a feedstock comprising a mixture of pentene-2 and n-pentane may be effected in the presence of a boron fluoride-alumina catalyst at similar reaction conditions after treating the catalyst with an oxygen or nitrogen-containing compound such as diethyl ether, dipropyl ether, methylamine or ethylamine to produce oligomers containing a greater amount of minimal branched isomers than may be obtained when effecting the oligomerization reaction without either pretreating the catalyst or treating the catalyst during the process with the aforementioned additives.

We claim as our invention:

1. In a process for the oligomerization of an olefin which contains from 2 to about 6 carbon atoms which comprises oligomerizing said olefin at oligomerization conditions in the presence of a catalyst comprising boron fluoride composited on an inorganic oxide, and recovering the resultant oligomer, the improvement which comprises treating said catalyst with an organic compound selected from the group consisting of ethers and amines.

2. The process of claim 1 in which said oligomerization conditions include a temperature in the range of from about 50° to about 300° C. and a pressure in the range of from about 100 to about 1500 pounds per square inch gauge.

3. The process of claim 1 in which said inorganic oxide is an alumina.

4. The process of claim 3 in which said alumina is gamma-alumina.

5. The process of claim 1 in which said inorganic oxide is silica-alumina.

6. The process of claim 1 in which said boron fluoride is present on said inorganic oxide in an amount in the range of from about 1% to about 10% by weight of said catalyst.

7. The process of claim 1 in which said olefin is propylene.

8. The process of claim 1 in which said olefin is butene-1 or butene-2.

9. The process of claim 8 in which said resultant oligomer is a mixture of methylheptene, dimethylhexene, and trimethylpentene.

10. The process of claim 1 in which said olefin is pentene-2.

11. The process of claim 10 in which said oligomer is a mixture of methylnonene, dimethyloctene and trimethylheptene.

12. The process of claim 1 in which said organic compound is dimethyl ether.

13. The process of claim 1 in which said organic compound is diethyl ether.

14. The process of claim 1 in which said organic compound is dipropyl ether.

15. The process of claim 1 in which said compound is methylamine.

16. The process of claim 1 in which said compound is ethylamine.

17. The process of claim 1 in which said catalyst is treated with from about 10 ppm to about 5% by weight of said organic compound.

18. The process of claim 1 in which said catalyst is treated with said organic compound prior to the start-up of said process.

19. The process of claim 1 in which said catalyst is treated with said organic compound in situ.

* * * * *